United States Patent [19]

Rosendahl

[11] Patent Number: 5,688,223

[45] Date of Patent: Nov. 18, 1997

[54] RETRACTOR SUPPORT WITH ADJUSTABLE RETRACTOR BLADES

[75] Inventor: Peter R. Rosendahl, Minneapolis, Minn.

[73] Assignee: Minnesota Scientific, Inc., Minneapolis, Minn.

[21] Appl. No.: 555,265

[22] Filed: Nov. 8, 1995

[51] Int. Cl.$^6$ ........................................... A61B 11/02
[52] U.S. Cl. ................ 600/215; 600/201; 600/205; 600/210; 600/214; 600/217; 600/224; 600/233
[58] Field of Search ........................... 600/201, 203, 600/206, 208, 210, 214, 215, 216, 217, 219, 224, 225, 227, 231, 233, 245, 246

[56] References Cited

U.S. PATENT DOCUMENTS

| | | | |
|---|---|---|---|
| 1,157,202 | 10/1915 | Bates et al. | 600/215 X |
| 1,400,616 | 12/1921 | McCrory et al. | 600/233 X |
| 1,706,500 | 3/1929 | Smith | 600/245 X |
| 2,623,517 | 12/1952 | Barlow et al. | 600/233 |
| 3,522,799 | 8/1970 | Gauthier | 600/215 |

Primary Examiner—Richard J. Apley
Assistant Examiner—Beverly M. Flanagan
Attorney, Agent, or Firm—Kinney & Lange, P.A.

[57] ABSTRACT

A retractor apparatus for use in conducting a surgical operation through an incision in a patient. The retractor includes a retractor support, a plurality of surgical retractors, and a stretchable sleeve. The surgical retractors are mounted to the retractor support such that at least two of the surgical retractors are facing each other. The stretchable sleeve encircles the surgical retractors to form a continuous surface around the surgical retractors for engagement of tissue.

32 Claims, 7 Drawing Sheets

RETRACTOR SUPPORT WITH ADJUSTABLE RETRACTOR BLADES

BACKGROUND OF THE INVENTION

The present invention relates to a surgical retractor apparatus. More particularly, the present invention relates to adjustable retractor blades on a retractor support.

When performing a surgical procedure a surgeon makes an incision in a patient. While it is desirable for the incision to be sufficiently large to provide a surgeon with unobstructed access when performing the surgical technique, it is also desirable to minimize the size of the incision to reduce discomfort to the patient as well as decrease recovery time.

Various surgical retractors have been developed to assist surgeons in gaining unobstructed access within the incision. The surgical retractors not only expand the size of the incision but also retract tissue or organs within the incision.

One common configuration for surgical retractors is to mount a plurality of surgical retractors to a circular retractor support ring. Mounting surgical retractors to the circular retractor support ring allows the surgeon to retract tissue and organs surrounding the incision. To prevent tissue and organs from moving between adjacent surgical retractors, the surgical retractors are selected to have a width that minimizes the spacing between the surgical retractors. Alternatively, a greater number of surgical retractors are placed in the incision to minimize the potential for tissue and organs from moving between adjacent surgical retractors.

SUMMARY OF THE INVENTION

The present invention includes a retractor apparatus for use in conducting a surgical operation through an incision made in a patient. The retractor apparatus has a retractor support ring, a plurality of surgical retractors, and a stretchable sleeve. The surgical retractors are mounted to the retractor support ring such that at least two of the retractors are facing each other. The stretchable sleeve encircles the surgical retractors to form a continuous surface around the surgical retractors for engagement of tissue within the incision.

DETAILED DESCRIPTION OF THE PREFERRED EMBODIMENTS

Figure 1:
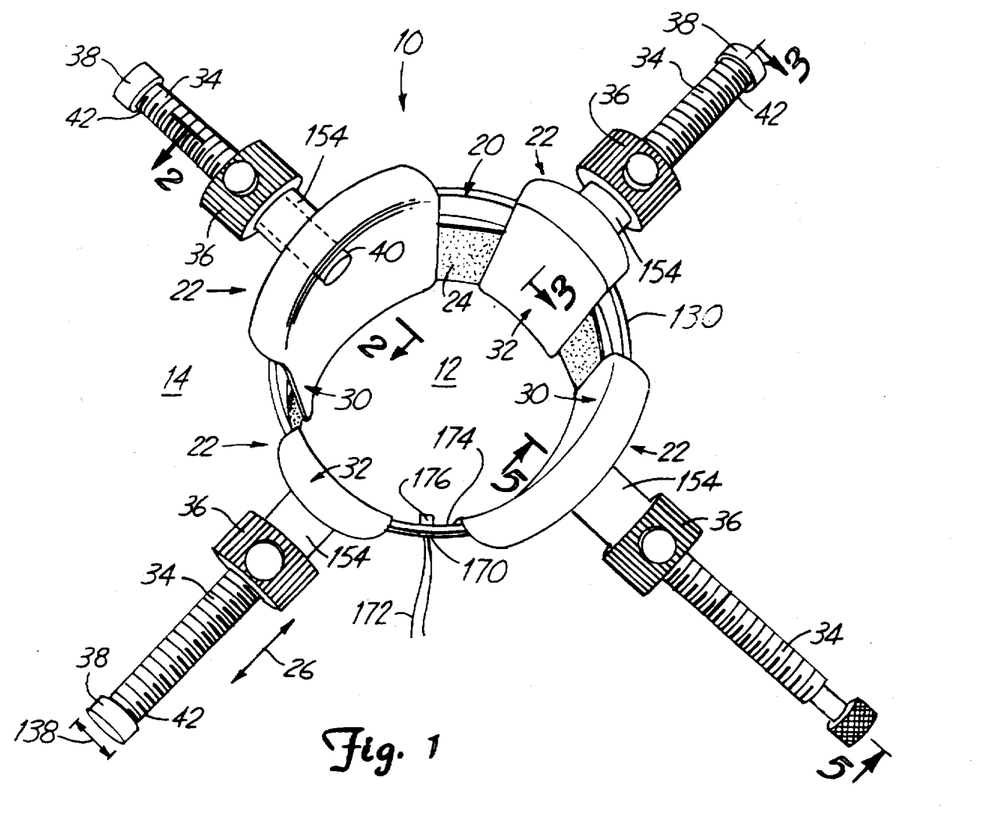
FIG. 1 is a perspective view of a retractor apparatus of the present invention in an open position.

The present invention includes a retractor apparatus as illustrated at 10 in FIG. 1. The retractor apparatus 10 is used in conducting a surgical operation through an incision 12 made in a patient 14. The retractor apparatus 10 includes a retractor support ring 20, a plurality of surgical retractors 22, and a stretchable sleeve 24. The retractor support ring 20 retains each of the surgical retractors 22 in a desired position with respect to the incision 12 so that a surgical opening may be formed from the incision 12.

Each of the surgical retractors 22 are mounted to the retractor support ring 20. Preferably, the surgical retractors 22 are mounted at approximately equal intervals around the retractor support ring 20. The mounting of the surgical retractors 22 to the retractor support ring 20 allows each of the surgical retractors 22 to independently move radially inwardly and outwardly with respect to the retractor support ring 20 as indicated by arrow 26.

The surgical retractors 22 are preferably selected with either a wide retractor blade 30 or a narrow retractor blade 32. When the retractor apparatus 10 includes four surgical retractors 22, two of the surgical retractors 22 are selected with the wide retractor blade 30 and two of the surgical retractors 22 are selected with the narrow retractor blade 32. The surgical retractors 22 with the wide retractor blade 30 are preferably oriented on the retractor support ring 20 opposite each other. Likewise, the surgical retractors 22 with the narrow retractor blade 32 are preferably oriented on the retractor support ring 20 opposite each other.

Each surgical retractor 22 preferably also includes a threaded rod 34, a radial adjustment controller 36, and a stop mechanism 38 for mounting the retractor blade 30, 32 to the retractor support ring 20. The threaded rod 34 has a proximal end 40 and a distal end 42. The threaded rod 34 is positioned so that the proximal end 40 extends through an aperture 44 in the retractor support ring 20, as most clearly illustrated in FIG. 2.

For purposes of this application, reference to horizontal refers to the typical position of the retractor support ring 20 and the threaded rod 34 lying in a substantially horizontal plane as illustrated in the drawings. However, the retractor support ring 20 and the threaded rod 34 may be positioned in a different manner when actually used depending on the surgical procedure.

Figures 2, 3:
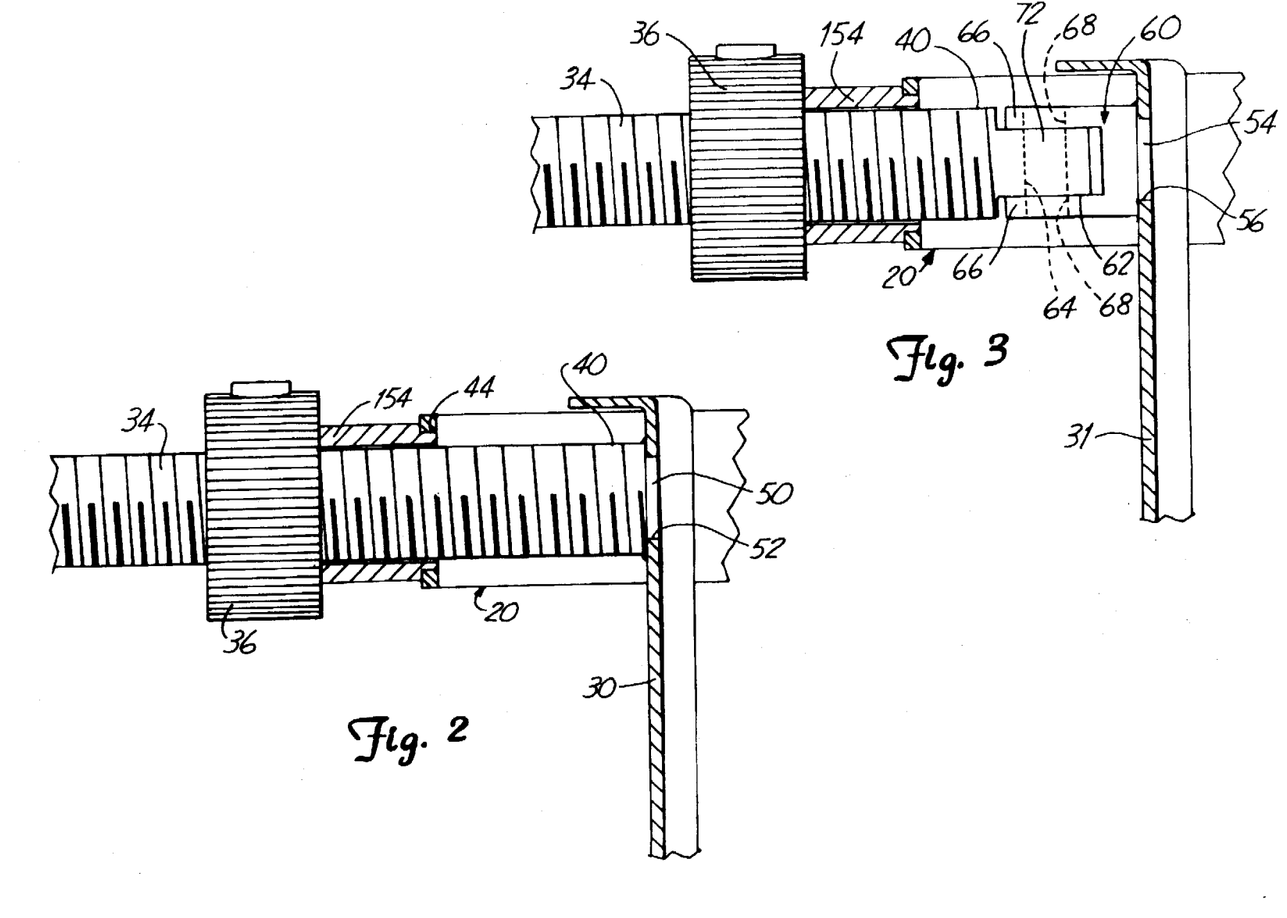
FIG. 2 is a sectional view of a retractor mounting structure, which is taken along a line 2—2 in FIG. 1.
FIG. 3 is a sectional view, which is taken along a line 3—3 in FIG. 1, illustrating a retractor mounted for side to side pivoting.

The wide retractor blade 30 is preferably fixedly mounted to the threaded rod 34, as most clearly illustrated in FIG. 2. The proximal end 40 of the threaded rod 34 preferably includes an annular projection 50. The wide retractor blade 30 has a circular aperture 52 that is adapted to receive the annular projection 50 for fixedly mounting the threaded rod 34 to the wide retractor blade 30.

The narrow retractor blade 32 is preferably pivotally mounted to the threaded rod 34 to allow the narrow retractor blade 32 to pivot side to side with respect to the threaded rod 34, as most clearly illustrated in FIG. 3. The narrow retractor blade 32 is preferably attached to the proximal end 40 of the threaded rod 34 using a blade swivel joint 60. The narrow retractor blade 32 is preferably fixedly mounted to the blade swivel joint 60. The blade swivel joint 60 preferably includes an annular projection 54. The narrow retractor blade 32 has a circular aperture 56 that is adapted to receive the annular projection 54 for fixedly mounting the blade swivel joint 60 to the narrow retractor blade 32.

The proximal end 40 of the threaded rod 34 includes a reduced diameter section 62. The reduced diameter section 62 has an aperture 64 disposed normally to an axis of the threaded rod 34.

The blade swivel joint 60 has two spaced-apart arm sections 66. The spaced-apart arm sections 66 form a recess adapted to receive the reduced diameter section 62. Each of the spaced-apart arm sections 66 includes an aperture 68. The apertures 68 on each of the spaced-apart area sections 66 are preferably axially aligned. The apertures 68 are also oriented on the spaced-apart arm sections 66 so that when the reduced diameter section 62 is placed between the spaced-apart arm sections 66, the apertures 68 are aligned with the aperture 64. The blade swivel joint 60 is retained in a pivotal relationship with respect to the threaded rod 34 by inserting a pivot pin 72 through the aligned apertures 64, 68.

Figure 4:
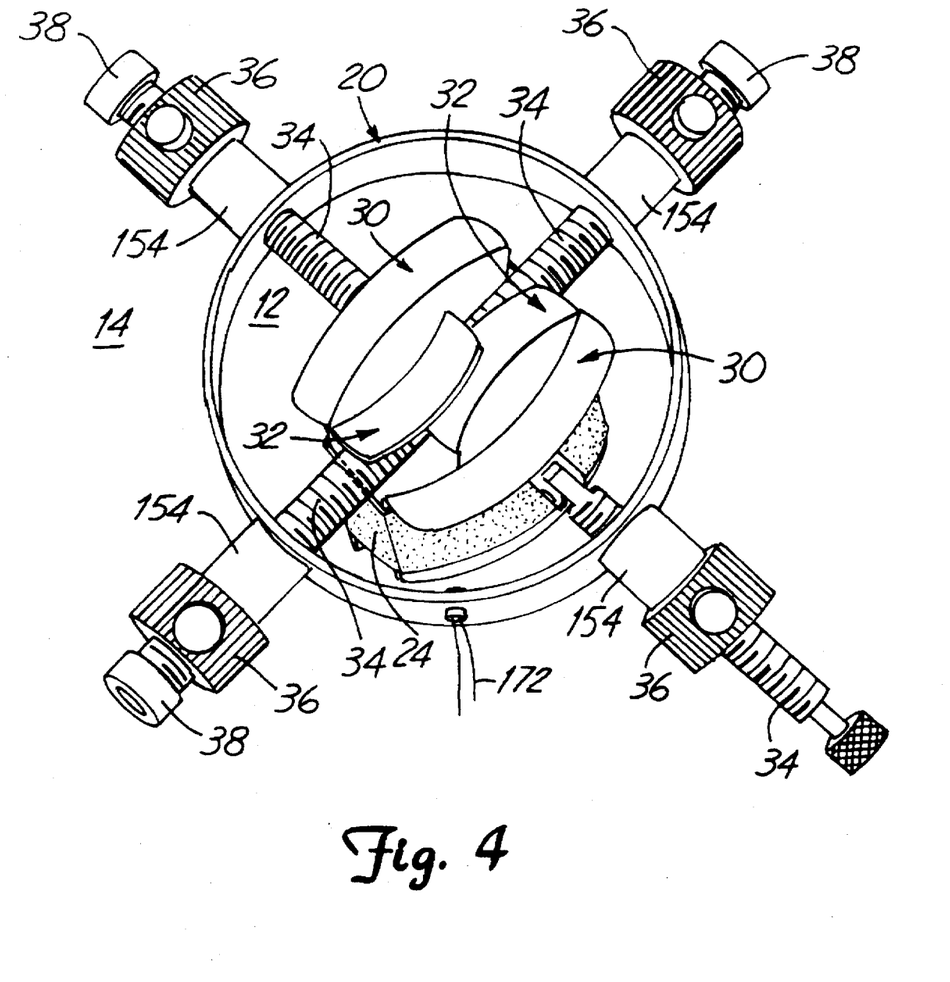
FIG. 4 is a perspective view of the retractor apparatus in a nested position.

Mounting the narrow retractor blades 32 for side to side pivoting with respect to the threaded rod 34 allows the narrow retractor blades 32 to nest between the wide retractor blades 30, as most clearly illustrated in FIG. 4. Nesting of the narrow retractor blades 32 between the wide retractor blades 30 allows the retractor blades 30, 32 to occupy a smaller profile than if the retractor blades 30, 32 did not nest. The capability of the narrow retractor blades 32 to pivot from side to side allows all of the retractor blades 30, 32 to nest more closely into a smaller profile. The smaller profile makes it easier to insert the retractor blades 30, 32 into the incision 12.

At least one of the wide retractor blades 30 is preferably mounted to the threaded rod 34 to allow the wide retractor blade 30 to pivot such that a vertical pitch of the wide retractor blade 30 is adjustable. As used herein, the term "vertical" means a plane that is normal to the substantially horizontal plane of the retractor support ring 20.

Figure 5:
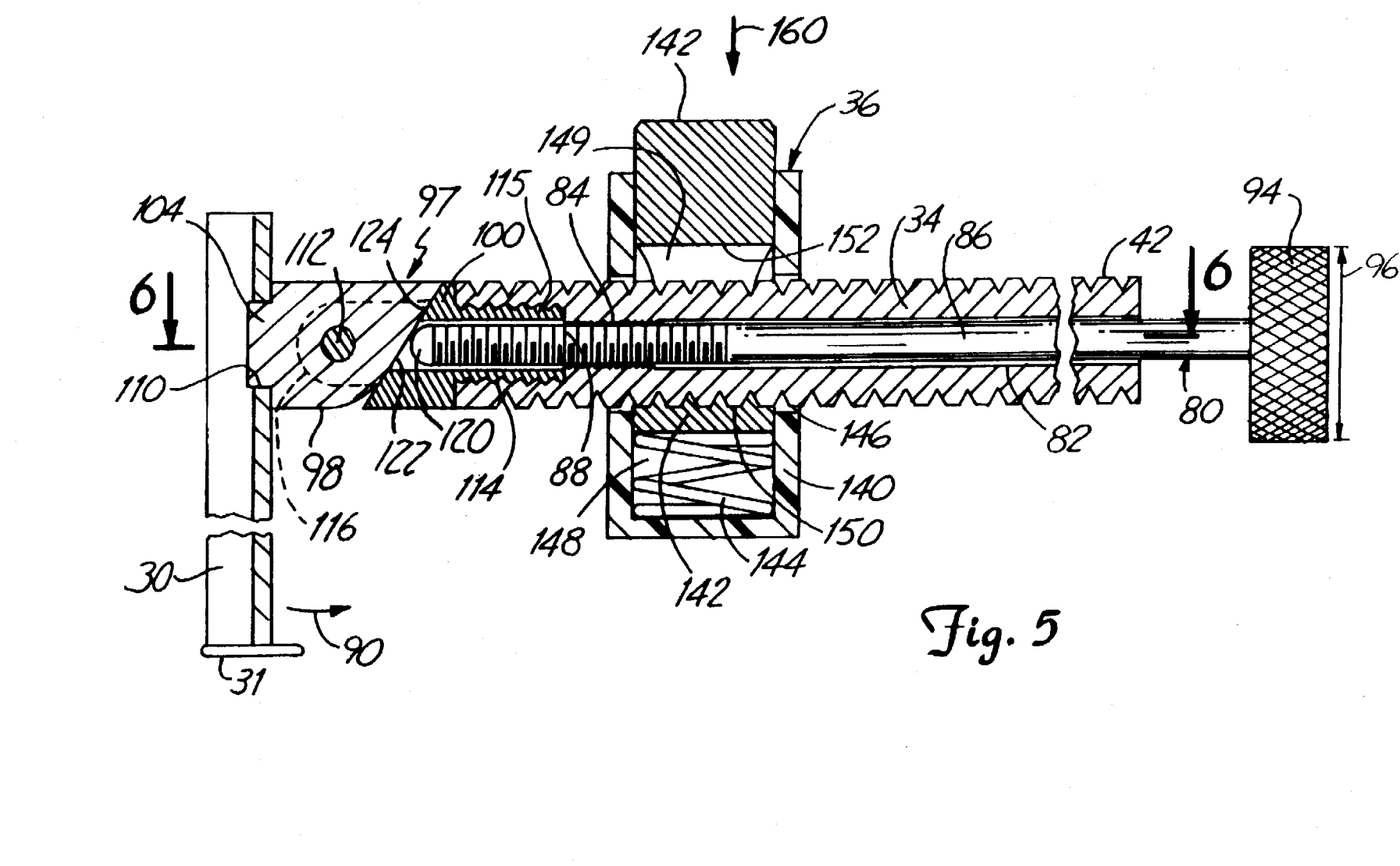
FIG. 5 is a sectional view, which is taken along a line 5—5 in FIG. 1, illustrating a retractor mounted for adjustment of a vertical pitch of the retractor.
Figure 6:
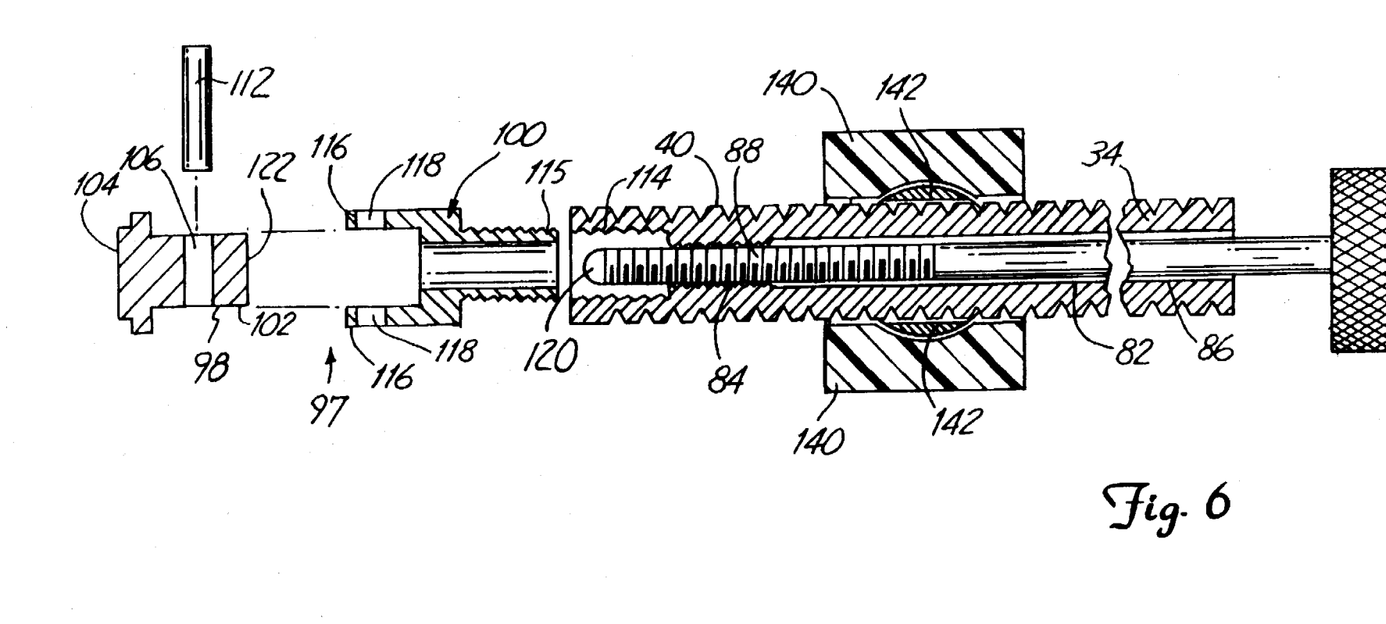
FIG. 6 is an exploded sectional view of the retractor, which is taken along a line 6—6 in FIG. 5.

More particularly, a lower portion 31 of the wide retractor blade 30 moves outwardly with respect to the retractor support ring 20 changing its pitch as most clearly illustrated in FIGS. 5 and 6. Vertically pivoting of the wide retractor blade 30 with respect to the threaded rod 34 allows a larger surgical opening to be formed inside the incision 12. The larger surgical opening increases a surgeon's field of view while allowing the tissue immediately surrounding the incision 12 to be expanded to a lesser extent.

The surgical retractor 22 preferably includes a pitch control mechanism 80 for controlling the vertical pitch of the wide retractor blade 30. The pitch control mechanism 80 includes a pitch control rod 86 with a male threaded region 88.

The threaded rod 34 includes a central bore 82 that is adapted to receive the pitch control rod 86. The central bore 82 includes a female threaded region 84 that is adapted to engage the male threaded region 88 on the pitch control rod 86. Rotation of the pitch control rod 86 with respect to the threaded rod 34 thereby causes the pitch control rod 86 to move axially with respect to the threaded rod 34 as indicated by arrow 90.

Rotation of the pitch control rod 86 is preferably controlled by a handle 94. The handle 94 preferably has a diameter 96 that is wider than the threaded rod 34 to retain the radial adjustment controller 36 in an assembled configuration with respect to the threaded rod 34.

The wide retractor blade 30 is removably mounted to the threaded rod 34 with a retractor mounting mechanism 97. The retractor mounting mechanism 97 includes a male pivot portion 98 and a female pivot portion 100. The male pivot portion 98 and the female pivot portion 100 are pivotally mounted together.

The male pivot portion 98 includes a reduced diameter portion 102 and an annular projection 104. The male pivot portion 98 also includes an aperture 106 disposed normally to a central axis of the male pivot portion 98. The wide retractor blade 30 has a circular aperture 110 that is adapted to receive the annular projection 104 for fixedly mounting the male pivot portion 98 to the wide retractor blade 30.

The proximal end 40 of the threaded rod 34 includes a female threaded region 114. The female threaded region 114 having a diameter that is greater than a diameter of the female threaded region 84.

The female pivot portion 100 includes a male threaded region 115 and two spaced-apart arm sections 116. The male threaded region 115 threadably engages the female threaded region 114 of the threaded rod 34 to removably attach the female pivot portion 100 to the threaded rod 34. Removably attaching the female pivot portion 100 to the threaded rod 34 allows the wide retractor blade 30 to be readily removed from the threaded rod 34.

The female pivot portion 100 also includes a central bore 117 extending therethrough. The central bore 117 is preferably axially aligned with the central bore 82 through the threaded rod 34 when the female pivot portion 100 threadably engages the threaded rod 34.

The spaced-apart arm sections 116 form a recess that is adapted to receive the reduced diameter portion 102. Each of the spaced-apart arm sections 116 includes an aperture 118. The apertures 118 on each of the spaced-apart arm sections 116 are preferably axially aligned. The apertures 118 are oriented on the spaced-apart arm sections 116 so that when the reduced diameter portion 102 is placed between the spaced-apart arm sections 116, the apertures 118 are aligned with the aperture 106. The female pivot portion 100 is retained in a pivotal relationship with respect to the male pivot portion 98 by inserting a pivot pin 112 through the apertures 106, 118.

The reduced diameter portion 102 of the male pivot portion 98 includes an angled surface 122. As the pitch control rod 86 is rotated with respect to the threaded rod 34, an end 120 of the pitch control rod 86 opposite the handle 94 contacts the pivot portion angled surface 122 and causes the male pivot portion 100 to vertically pivot with respect to the female pivot portion 98.

Preferably, the female pivot portion 100 includes an angled surface 124 that conforms with the pivot portion angled surface 122. Contact between the angled surface 124 and the pivot portion angled surface 122 limits the extent to which the male pivot portion 98 may pivot with respect to the female pivot portion 100.

Figure 7:
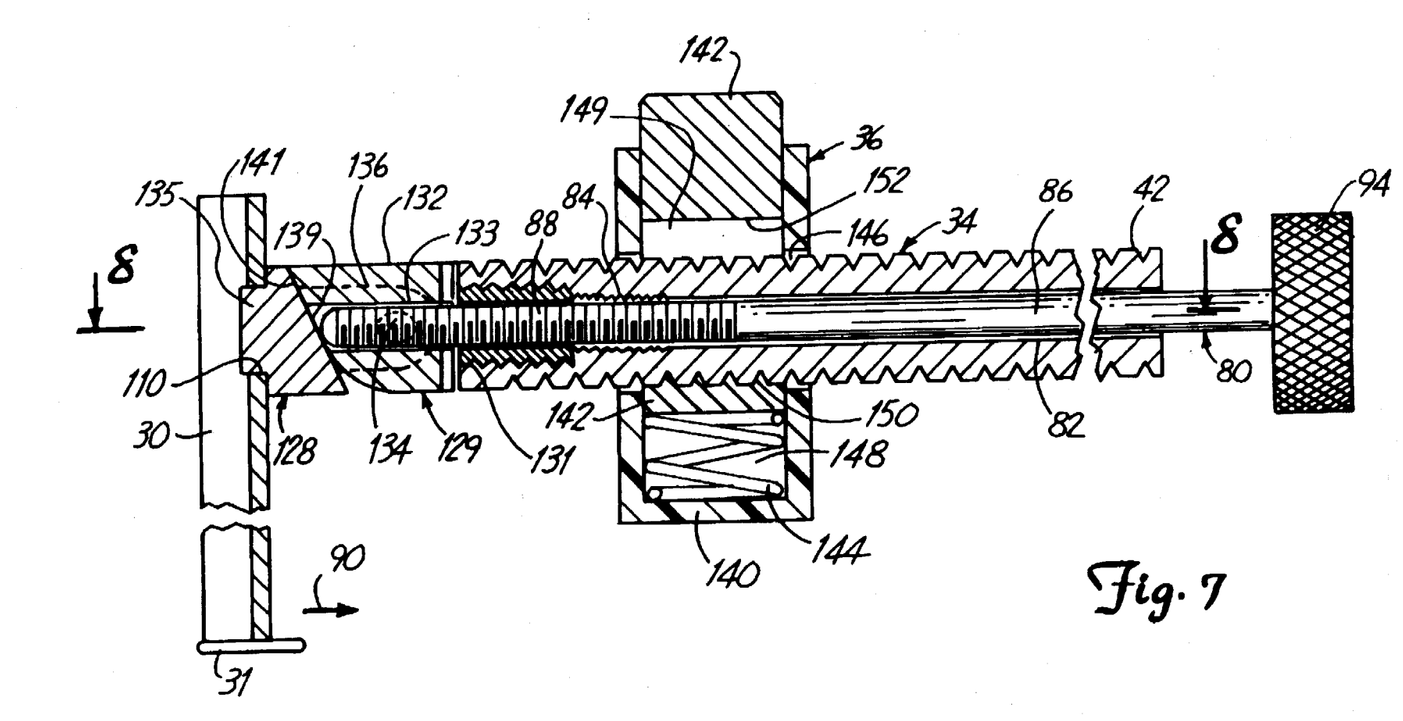
FIG. 7 is a sectional view illustrating an alternative mechanism for mounting a retractor for adjustment of a vertical pitch of the retractor.
Figure 8:
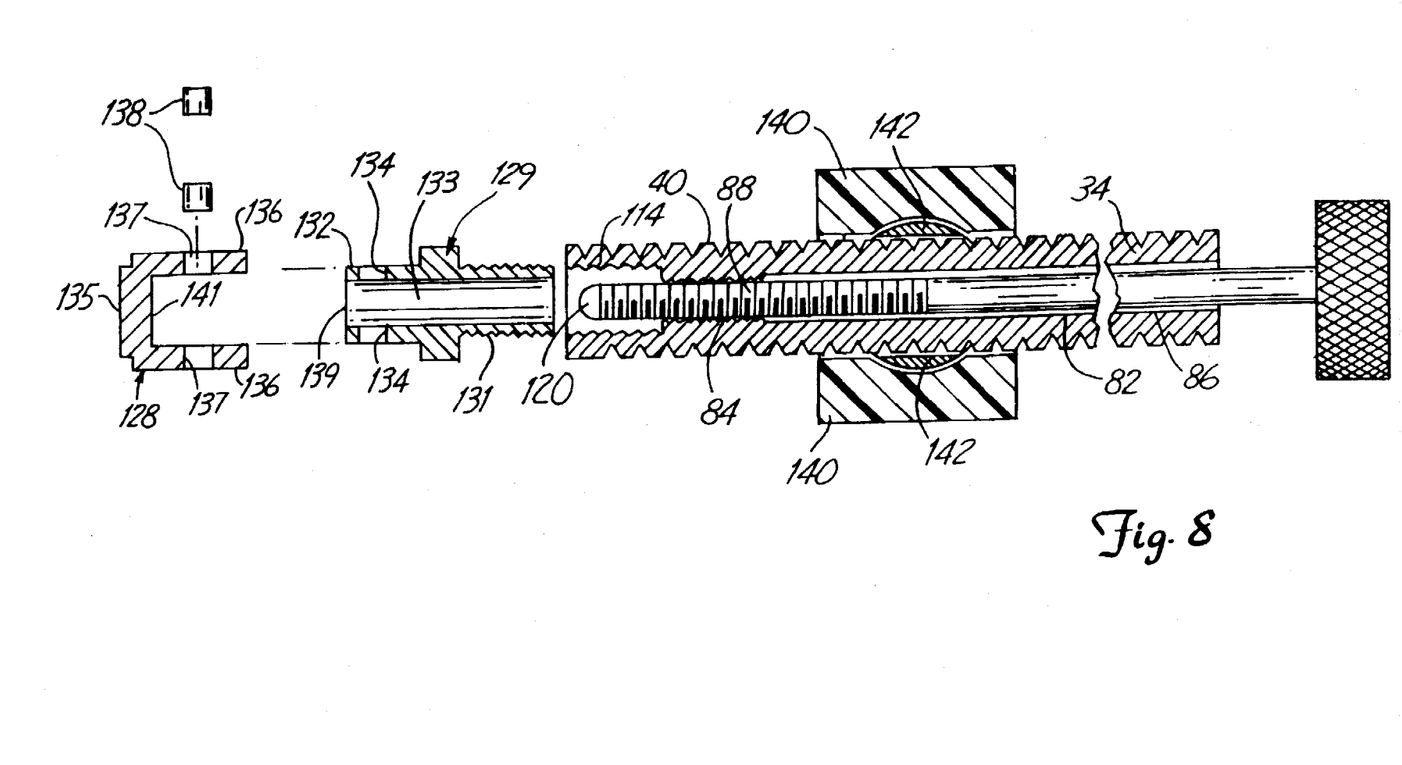
FIG. 8 is an exploded sectional view of the retractor, which is taken along a line 8—8 in FIG. 7.

The present invention also includes an alternative mounting mechanism 126 for mounting the wide retractor blade 30 to the threaded rod 34, as most clearly illustrated in FIGS. 7 and 8. Similar to the mounting mechanism 97 illustrated in FIGS. 5 and 6, the alternative mounting mechanism 126 removably mounts the wide retractor blade 30 to the threaded rod 34. The mounting mechanism 126 includes a male pivot portion 129 and a female pivot portion 128. The male pivot portion 129 and the female pivot portion 129 are pivotally mounted together.

The male pivot portion 129 includes a male threaded region 131 and a reduced diameter portion 132. The male pivot portion 129 also includes an aperture 134 disposed normally to a central axis of the male pivot portion 129. The male threaded region 131 threadably engages the female threaded region 114 of the threaded rod 34 to removably attach the male pivot portion 129 to the threaded rod 34. Removably attaching the male pivot portion 129 to the threaded rod 34 allows the wide retractor blade 30 to be readily removed from the threaded rod 34.

The male pivot portion 129 also includes a central bore 133 extending therethrough. The central bore 133 is preferably axially aligned with the central bore 82 through the threaded rod 34 when the male pivot portion 129 threadably engages the threaded rod 34.

The female pivot portion 128 includes an annular projection 135 and two spaced-apart arm sections 136. The circular aperture 110 in the wide retractor blade 30 is adapted to receive the annular projection 135 for fixedly mounting the female pivot portion 128 to the wide retractor blade 30.

The spaced-apart arm sections 136 form a recess that is adapted to receive the reduced diameter portion 132. Each of the spaced-apart arm sections 136 includes an aperture 137. The apertures 137 on each of the spaced-apart arm sections 136 are preferably axially aligned. The apertures 137 are also oriented on the spaced-apart arm sections 136 so that when the reduced diameter portion 132 is placed between the spaced-apart arm sections 136, the apertures 137 are aligned with the aperture 134. The female pivot portion 128 is retained in a pivotal relationship with respect to the male pivot portion 129 by inserting pivot pins 138 through the apertures 134, 137 on each side of the central bore 133.

The recess between the spaced-apart arm sections 136 includes an angled surface 139. As the pitch control rod 86 is rotated with respect to the threaded rod 34, the end 120 of the pitch control rod contacts the angled surface 139 and causes the female pivot portion 128 to vertically pivot with respect to the male pivot portion 129.

Preferably, the male pivot portion 129 includes an angled surface 141 that conforms with the angled surface 139. Contact between the angled surface 139 and the angled surface 141 limits the extent to which the female pivot portion 128 may pivot with respect to the male pivot portion 129.

It is understood that a person of ordinary skill in the art will readily appreciate that the narrow retractor blades 32 may be mounted for both side to side pivoting and vertical pitch adjustment and that each of the retractor blades 30, 32 may be removably mounted to the threaded rods 34.

The radial adjustment controller 36 controls radial movement of the threaded rod 34 with respect to the retractor support ring 20 as indicated by arrow 26 in FIG. 1. The radial adjustment controller 36 engages the threaded rod 34 between the proximal end 40 and the distal end 42 proximate to an exterior surface 130 of the retractor support ring 20.

The radial adjustment controller 36 is capable of operating in a fine adjustment mode and a coarse adjustment mode. The radial adjustment controller 36 is preferably biased in the fine adjustment mode.

The structure of the radial adjustment controller 36 is most clearly illustrated in FIGS. 5 and 6. The radial adjustment controller 36 includes a casing portion 140, an engagement portion 142, and a spring 144. The casing portion 140 includes an aperture 146 through which the threaded rod 34 is disposed. The casing portion 140 also includes a recess 148 that is adapted to receive at least a portion of the engagement portion 142 and the spring 144.

The engagement portion 142 includes an aperture 149 through which the threaded rod 34 is disposed. The aperture has a threaded surface section 150 and a substantially smooth surface section 152.

The spring 144 biases the engagement portion 142 so that the threaded surface section 150 engages the threaded rod 34. When the threaded surface section 150 engages the threaded rod 34, the radial adjustment controller 36 is in the fine adjustment mode and the position of the surgical retractor 22 may be radially adjusted by rotating the radial adjustment controller 36 with respect to the threaded rod 34.

When it is desired to radially adjust the position of the surgical retractor 22 more quickly, the radial adjustment controller 36 is moved to the coarse adjustment mode. The coarse adjustment mode is entered by moving the engagement portion 142 with respect to the casing portion 140 as indicated by arrow 160 in FIG. 5 so that the threaded rod 34 is adjacent to the substantially smooth surface section 152. When the threaded rod 34 is adjacent to the substantially smooth surface section 152, the threaded surface section 150 does not engage the threaded rod 34.

The retractor apparatus 10 preferably also includes at least one spacer 154 mounted to the retractor support ring 20, as most clearly illustrated in FIG. 1. The spacer 154 retains the radial adjustment controller 36 a selected distance from the retractor support ring 20. The spacer 154 minimizes interference between the radial adjustment controller 36, the retractor support ring 20 or the retractor blades 30, 32 when adjusting the radial position of the retractor blades 30, 32.

The surgical retractors 22 are preferably retained in an assembled configuration with respect to the retractor support ring 20 by the stop mechanism 38, as most clearly illustrated in FIG. 1. Maintaining the surgical retractors 22 in the assembled configuration is desirable to prevent components of the retractor apparatus 10 from being lost during use or cleaning.

The stop mechanism 38 is mounted to the distal end 42 of the threaded rod 34. The stop mechanism 38 has an outer diameter 148 that is greater than the width of the aperture 146 in the casing portion 140. The stop mechanism 38 thereby prevents the radial adjustment controller 36 from becoming detached from the threaded rod 34. By preventing the radial adjustment controller 36 from becoming detached from the threaded rod 34, the stop mechanism 38 thereby retains the surgical retractor 22 on the retractor support ring 20.

The stretchable sleeve 24 is placed over the retractor blades 30, 32 so that the stretchable sleeve 24 encircles the retractor blades 30, 32. The stretchable sleeve 24 thereby forms a continuous surface between the retractor blades 30, 32 and prevents tissue and organs within the incision 12 from interfering with the surgical operation. Because the stretchable sleeve 24 forms a continuous surface between the retractor blades 30, 32, the retractor blades 30, 32 may be selected with narrower widths than previously possible with prior art retractor apparatuses. Forming the retractor blades 30, 32 with narrower widths allows the retractor blades 30, 32 to nest into a smaller profile, which reduces the size of the incision 12 that must be made in the patient. The stretchable sleeve 24 is preferably made of a material that is also pliant, such as latex or a silicone elastomer.

With prior art retractor apparatus that did not include the stretchable sleeve, the retractor blades were required to be wider than the retractor blades used with the present invention to prevent tissue and organs within the incision from interfering with the surgical operation. A drawback of using wider retractor blades is that the incision must be larger than the incision made to insert the retractor blades 30, 32 of the present invention.

The retractor apparatus 10 is preferably free-floating in the incision 12. As used herein, the term "free floating" means that the retractor apparatus 10 is not maintained in the incision 12 by mounting either directly or indirectly to an operating table (not shown).

The retractor apparatus 10 may also be used in conjunction with a support apparatus (not shown) to retain the retractor apparatus in a stationary position over the patient who is positioned on the operating table. The support apparatus is typically attached to side rails (not shown) that are mounted along sides of the operating table with a side rail clamping device. A suitable support apparatus and side rail clamping device is described in U.S. Pat. No. 4,355,631, which is assigned to the assignee of the present application and is hereby incorporated by reference.

The retractor support ring 20 also preferably includes a port 170 for attachment of a light source 172, such as a fiber optic cable, to the retractor support ring 20. The port 170 preferably allows the light source 172 to be quickly connected and disconnected from the retractor support ring 20. The port 170 also preferably includes a mirror 176 that is mounted proximate to an interior surface 174 of the retractor support ring 20. The mirror 176 reflects light that is delivered from the light source 172 into the incision 12.

Although the present invention has been described with reference to preferred embodiments, workers skilled in the art will recognize that changes may be made in form and detail without departing from the spirit and scope of the invention.

What is claimed is:

1. A retractor apparatus for use in conducting a surgical operation through an incision made in a patient, the retractor apparatus comprising:
    a retractor support; and
    a plurality of surgical retractors mounted to the retractor support such that at least two of the surgical retractors are facing each other, wherein at least one surgical retractor comprises;
        a threaded rod mounted to the retractor support;
        a retractor blade mounted to the threaded rod; and
        an adjusting mechanism for adjusting the threaded rod radially with respect to the retractor support, wherein the adjusting mechanism includes an engagement portion having an aperture that is capable of receiving the threaded rod, wherein the aperture has a threaded surface section and a smooth surface section.

2. The retractor apparatus of claim 1 wherein each surgical retractor comprises:
    a retaining mechanism for retaining the threaded rod and the adjusting mechanism in an assembled configuration with respect to the retractor support.

3. The retractor apparatus of claim 2 wherein the plurality of surgical retractors includes a first pair of surgical retractors and a second pair of surgical retractors, and wherein the second pair of surgical retractors is nestable between the first pair of surgical retractors when the first pair of surgical retractors and the second pair of surgical retractors are radially moved toward a central axis of the retractor support.

4. The retractor apparatus of claim 3 wherein each of the retractor blades in the second pair of surgical retractors is pivotable side to side with respect to the threaded rod to which the retractor blade is mounted.

5. The retractor apparatus of claim 2 wherein the retractor blade is pivotable with respect to the threaded rod to which the retractor blade is mounted to adjust a pitch of the retractor blade.

6. The retractor apparatus of claim 5 and further comprising a pitch control mechanism for adjusting the pitch of the retractor blade.

7. The retractor apparatus of claim 6 wherein the retractor blade is attached to the threaded rod with a blade swivel joint, the blade swivel joint being mounted to the retractor blade and having an angled surface opposite the retractor blade, wherein the threaded rod includes a central bore, and wherein the pitch control mechanism comprises a pitch control rod extending through the central bore and contacting the angled surface.

8. The retractor apparatus of claim 1 wherein the adjusting mechanism is in a fine adjustment mode when the threaded surface section is adjacent to the threaded rod and wherein the adjusting mechanism is in a coarse adjustment mode when the substantially smooth section is adjacent to the threaded rod.

9. The retractor apparatus of claim 8 wherein the adjusting mechanism is biased to the fine adjustment mode.

10. The retractor apparatus of claim 9 wherein the adjusting mechanism comprises:
    a casing portion having an aperture that is capable of receiving the threaded rod; and
    a spring portion for biasing the threaded surface section of the engagement portion in communication with the threaded rod.

11. The retractor apparatus of claim 1 wherein the retractor support includes a port that is adapted to receive a light source.

12. The retractor apparatus of claim 11 wherein the port includes a directing mechanism for directing light from the light source into the incision.

13. The retractor apparatus of claim 1, and further comprising a stretchable sleeve encircling the surgical retractors to form a continuous surface around the surgical retractors for engagement of tissue.

14. A retractor apparatus for use in conducting surgical operations through an incision in a patient, the retractor apparatus comprising:
    a retractor support;
    a first pair of surgical retractors mounted to the retractor support for radial movement within the retractor support, wherein the first pair of surgical retractors each comprise:
        a first threaded rod mounted to the retractor support; and
        a first retractor blade mounted to the first threaded rod; and
    a second pair of surgical retractors mounted to the retractor support for radial movement within the retractor support, wherein the second pair of surgical retractors each comprise:
        a second threaded rod mounted to the retractor support; and
        a second retractor blade pivotally mounted to the second threaded rod so that the second retractor blades are pivotable side to side with respect to the second threaded rod to which the second retractor blade is mounted, wherein pivoting the second retractor blades permits the second retractor blades to nest between the first retractor blades when the first and second retractor blades are radially moved toward a central axis of the retractor support and thereby reduces a profile of the first and second retractor blades when the first and second retractor blades are in a nested position.

15. The retractor apparatus of claim 14 wherein each surgical retractor in the first pair of surgical retractors comprises:
    an adjusting mechanism for adjusting the first threaded rod radially with respect to the retractor support; and
    a retaining mechanism for retaining the first threaded rod and the adjusting mechanism in an assembled configuration with respect to the retractor support.

16. The retractor apparatus of claim 15 wherein the first retractor blades are selected with a width that is greater than the second retractor blades.

17. The retractor apparatus of claim 15 wherein the adjusting mechanism comprises:
   a casing portion having an aperture that is capable of receiving the first threaded rod;
   an engagement portion operable within at least a portion of the casing portion, the engagement portion having an aperture that is capable of receiving the first threaded rod, the aperture having a threaded surface section and a substantially smooth surface section; and
   a spring portion for biasing the threaded surface section of the engagement portion in communication with the first threaded rod.

18. The retractor apparatus of claim 15 wherein at least one of the first retractor blades is pivotable with respect to the first threaded rod to which the first retractor blade is mounted to adjust a pitch of the first retractor blade.

19. The retractor apparatus of claim 18 and further comprising a pitch control mechanism for adjusting the pitch of the first retractor blade.

20. The retractor apparatus of claim 19 wherein the first retractor blade is attached to the first threaded rod with a blade swivel joint, the blade swivel joint being mounted to the first retractor blade and having an angled surface opposite the first retractor blade, wherein the first threaded rod includes a central bore, and wherein the pitch control mechanism comprises a pitch control rod extending through the central bore and contacting the angled surface.

21. The retractor apparatus of claim 13 and further comprising a stretchable sleeve encircling the surgical retractors to form a continuous surface between the surgical retractors for retraction of tissue within the incision.

22. The retractor apparatus of claim 13 wherein the retractor support includes a port that is adapted to receive a light source.

23. The retractor apparatus of claim 22 wherein the port includes a directing mechanism for directing light from the light source into the incision.

24. A retractor apparatus for use in conducting surgical operations through an incision in a patient, the retractor apparatus comprising:
   a retractor support; and
   a plurality of surgical retractors mounted to the retractor support, at least one surgical retractor comprising:
     a threaded rod mounted to the retractor support, wherein the threaded rod has a first end and a second end;
     a retractor blade mounted to the first end of the threaded rod, wherein the retractor blade is pivotable with respect to the threaded rod to adjust a pitch of the retractor blade; and
     a pitch control mechanism for adjusting the pitch of the retractor blade, wherein the control mechanism includes a handle mounted with respect to the threaded rod proximate to the second end of the threaded rod, and wherein the handle permits the pitch of the retractor blade to be adjusted.

25. The retractor apparatus of claim 24 and further comprising:
   an adjusting mechanism for adjusting the threaded rod radially with respect to the retractor support; and
   a retaining mechanism for retaining the threaded rod and the adjusting mechanism in an assembled configuration with respect to the retractor support.

26. The retractor apparatus of claim 25 wherein the adjusting mechanism comprises:
   a casing portion having an aperture that is capable of receiving the threaded rod;
   an engagement portion operable within at least a portion of the casing portion, the engagement portion having an aperture that is capable of receiving the threaded rod, the aperture having a threaded surface section and a substantially smooth surface section; and
   a spring portion for biasing the threaded section of the engagement portion in communication with the threaded rod.

27. The retractor apparatus of claim 25 wherein the plurality of surgical retractors includes a first pair of surgical retractors and a second pair of surgical retractors, and wherein the second pair of surgical retractors is nestable within the first pair of surgical retractors when the first pair of surgical retractors and the second pair of surgical retractors are radially moved toward a central axis of the retractor support for facilitating insertion of the surgical retractors within the incision.

28. The retractor apparatus of claim 27 wherein each of the retractor blades in the second pair of surgical retractors is pivotable side to side with respect to the threaded rod to which the retractor blade is mounted.

29. The retractor apparatus of claim 25 wherein the retractor blade is mounted to the threaded rod with a blade swivel joint, the blade swivel joint being mounted to the retractor blade and having an angled surface opposite the retractor blade, wherein the threaded rod includes a central bore, and wherein the pitch control mechanism comprises a pitch control rod extending through the central bore and contacting the angled surface.

30. The retractor apparatus of claim 25 and further comprising a stretchable sleeve encircling the surgical retractors to form a continuous surface around the surgical retractors for engagement of tissue.

31. The retractor apparatus of claim 25 wherein the retractor support includes a port that is adapted to receive a light source.

32. The retractor apparatus of claim 31 wherein the port includes a directing mechanism for directing light from the light source into the incision.

* * * * *

UNITED STATES PATENT AND TRADEMARK OFFICE
CERTIFICATE OF CORRECTION

PATENT NO. : 5,688,223
DATED : NOVEMBER 18, 1997
INVENTOR(S) : PETER R. ROSENDAHL

It is certified that error appears in the above-indentified patent and that said Letters Patent is hereby corrected as shown below:

Col. 3, line 3, delete "area", insert --arm--

Signed and Sealed this

Eighth Day of September, 1998

Attest:

BRUCE LEHMAN

Attesting Officer

Commissioner of Patents and Trademarks